United States Patent [19]
Inoue et al.

[11] Patent Number: 5,372,997
[45] Date of Patent: Dec. 13, 1994

[54] ALBUMIN PREPARATION AND METHOD FOR PRESERVING THE SAME

[75] Inventors: Masahiro Inoue; Hirokazu Ito; Shinji Tomioka; Sadao Yabushita; Koei Ikariya; Kohichi Furuta, all of Osaka, Japan

[73] Assignee: The Green Cross Corporation, Osaka, Japan

[21] Appl. No.: 66,157

[22] PCT Filed: Nov. 29, 1991

[86] PCT No.: PCT/JP91/01675
§ 371 Date: May 28, 1993
§ 102(e) Date: May 28, 1993

[87] PCT Pub. No.: WO92/09303
PCT Pub. Date: Jun. 11, 1992

[30] Foreign Application Priority Data

Nov. 30, 1990 [JP] Japan .................................. 2-339949

[51] Int. Cl.$^5$ ...................... A61K 37/00; B65D 23/00
[52] U.S. Cl. ............................ 514/21; 215/DIG. 3; 530/362; 530/363; 530/364; 436/88; 435/296
[58] Field of Search ............... 514/21; 530/362, 363, 530/364; 426/656; 436/88; 435/296; 422/102; 604/232; 215/DIG. 3

[56] References Cited

U.S. PATENT DOCUMENTS 3,598,269  8/1971  Carmen ................. 215/1 C
3,746,196  7/1973  Sako et al. ............ 215/1 C

FOREIGN PATENT DOCUMENTS 0367220  10/1989  European Pat. Off. ....... C07K 3/20
0428758   5/1991  European Pat. Off. ...... A61K 37/02
59-152245  8/1984  Japan ..................... C03C 23/00
61-236635 10/1986  Japan ..................... C03C 23/00
WO9100290  1/1991  WIPO ..................... C07K 3/12

OTHER PUBLICATIONS

The Second Series of Pharmaceutical Research and Development, vol. 9, Package and Container Drugs, ed. by H. Sezaki, M. Sugihara, p. 351 Hirokawa Publishing Co. (1991).

Victor et al., "Aluminum contamination in albumin solutions . . . ", Transfusion, 28(3), pp. 290–291 (1988).

*Primary Examiner*—Michael G. Wityshyn
*Assistant Examiner*—C. Sayala
*Attorney, Agent, or Firm*—Sughrue, Mion, Zinn, Macpeak & Seas

[57] ABSTRACT

It has been found that aluminum, which is considered as to cause various diseases such as dialysis dementia, bone diseases, hypochromic anemia and Alzheimer's disease, would be eluted into a conventional albumin preparation preserved in a hard glass container, which increases the aluminum concentration of the preparation. According to the present invention, it has been found that the substitution of the conventional hard glass container with a soft glass container dealkalized by, for example, treatment with sulfurous acid gas or ammonium sulfate solution for preserving an albumin preparation can make it possible to prevent the elution of aluminum from the container, thus giving a highly safe albumin preparation which can be maintained with an extremely low aluminum concentration over a long period of time.

11 Claims, No Drawings

ALBUMIN PREPARATION AND METHOD FOR PRESERVING THE SAME

TECHNICAL FIELD

This invention relates to an albumin preparation and a method for preserving the same. More particularly, it relates to a liquid preparation of albumin of plasma origin and a method for preserving the same whereby an increase in the aluminum content of said preparation during storage is avoided.

TECHNICAL BACKGROUND

Serum albumin, the most abundant protein in plasma, contributes to the maintenance of osmotic pressure and binds to and transports nutrients and metabolites. Preparations containing the above-mentioned albumin have been used in the treatment of hypoalbuminemia and hemorrhagic shock due to a loss of albumin or in the ability to synthesize albumin.

Generally, albumin preparations are prepared from plasma via several purification stages. During detailed studies on contaminants of albumin preparations, the present inventors found that albumin preparations contain a significantly large amount of aluminum.

In recent years, attention has been directed to the correlation between aluminum and various diseases. For example, it is believed that bone diseases accompanied by serious pain, which are observed frequently in patients experiencing hemodialysis or prolonged instillation, are caused by aluminum contained in solutions employed in those treatments.

It is considered, furthermore, that dialysis dementia, bone diseases and hypochromic anemia observed in patients undergoing hemodialysis for treating chronic renal insufficiency are caused by the accumulation of aluminum in serum.

In addition, the correlation between aluminum in brain tissue and Alzheimer's disease (senile dementia) has attracted attention.

In view of those observations, attempts have been made world-wide to control the aluminum content of medical preparations.

There are a variety of hard glasses (borosilicate glass; falling within Class I in the Glass Classification of USP) and soft glasses (soda-lime glass, falling within Class II in the Glass Classification of USP) having a dealkalized surface which serve as materials of containers for injectable materials. Soft glass has a low melting point, can be easily molded and is less expensive than hard glass. These materials differ from each other in other physical properties, including chemical resistance. Thus different glasses have been used depending on the drugs to be contained. Hard glass containers are usable for preserving acidic, neutral or alkaline drug-containing solutions. On the other hand, soft glass containers are usable for preserving acidic and neutral drug-containing solutions, whereas the suitability for storing alkaline drug-containing solutions must be confirmed.

Hard glass containers which are excellent in chemical resistance have been employed conventionally and uniformly for preserving albumin preparations.

DISCLOSURE OF THE INVENTION

The present inventors have conducted extensive studies to reduce the aluminum content of an albumin preparation. As a result, the instant inventors found that a significantly high aluminum content of the final product is attributed to the contamination of the albumin preparation with aluminum during the production stage of the albumin preparation. Thus the present inventors have found that the aluminum content can be reduced by treating an albumin-containing aqueous solution with an anion exchanger during preparation.

It also has been found that when a liquid albumin preparation in which the aluminum content has been reduced by such a purification method is preserved in a conventional hard glass container, the aluminum content of the preparation increases during storage.

The present invention has been achieved to solve those problems. It is an object of the present invention to provide an albumin preparation, wherein an increase in the aluminum content thereof during preparation is minimized, and a method for preserving the same.

The present inventors further have studied methods for preserving an albumin preparation. As a result, they have found that the aluminum content of an albumin preparation can be maintained at a low level by using a soft glass container with a dealkalized surface as a preservation container. The present invention has been completed based on those findings and provides an aqueous solution containing albumin of plasma origin which is preserved in a dealkalized soft glass container.

The present invention is described in detail below.

1. Albumin-containing Aqueous Solution

The albumin-containing aqueous solution to be used in the present invention is not restricted so long as it is usable as a drug. To achieve the object of the present invention, namely, the reduction of aluminum content of the preparation, it is preferable to use an aqueous solution of albumin of plasma origin which has been treated with an anion exchanger so as to eliminate the contaminating aluminum and, if required, further purified with the use of a cation exchanger. The purification method is hereinafter described in detail.

(1) Starting Material

The origin of the albumin to be used as the starting material in the present invention is not restricted. Particularly, those originating from mammalian (for example, human, bovine or rabbit) are usable. It is preferable to use albumin of human origin. As a starting material for preparing albumin, the fraction V obtained by Cohn's cold-alcohol fractionation method is usable.

(2) Treatment with Anion Exchanger

The amino exchange treatment may be effected by dissolving the above-mentioned albumin in a suitable purified water and then contacting the albumin-containing aqueous solution thus obtained with an anion exchanger.

The albumin concentration of the albumin-containing aqueous solution may be adjusted usually to from 0.1 to 30% (w/v, the same shall apply hereinafter unless otherwise noted), preferably from approximately 1 to 10%.

As the anion exchanger, any insoluble carrier having a anion exchanging group (for example, quaternary alkylammonium base or diethylaminoethyl group) may be used. More particularly, anion exchangers commonly employed in the art, for example, DEAE-SEPHAROSE ® (agarose bead matrix comprising the diethylaminoethy functional group), Q-SEPHAROSE ® (agarose bead matrix comprising the $CH_2N^+(CH_3)_3$ functional group) (each a product of Pharmacia), DEAE-TOYOPEARL ® (a vinyl polymer bead matrix comprising the diethylaminoethyl functional group), QAE-TOYOPEARL ® (a vinyl polymer bead matrix comprising the diethyl[2-hydroxypropyl]aminoethyl functional group), (each a product of Tosoh Co.), A200 CELLULOFINE ® (a cellulose bead matrix comprising the diethylaminoethyl functional group) (a product of Seikagaku Co.) and other known anion exchange resins may be used. From the viewpoint of the efficiency for eliminating aluminum, it is preferable to use strong anion exchangers, such as Q-SEPHAROSE ® and QAE-TOYOPEARL ®.

The treatment with the above-mentioned anion exchanger may be carried out by contacting the albumin-containing aqueous solution with the anion exchanger. The amount of the anion exchanger may be controlled appropriately depending on the aluminum content of the albumin-containing aqueous solution, the amount of contaminating proteins and the exchanging capacity of the anion exchanger. In general, from 2 to 5 ml, usually about 3 ml, of the anion exchanger is used per gram of albumin. The treatment may be effected either by the column method or by the batch method. The column method is preferable from the viewpoint of the efficiency of eliminating aluminum.

In the case of the column method, the above-mentioned albumin-containing aqueous solution is adjusted to a pH value of from 3 to 6, preferably from 4.5 to 5.5, and to a salt concentration of from 0.001 to 0.2M, preferably from 0.001 to 0.05M, in terms of sodium chloride. Then the solution is passed through an anion exchange column equilibrated with a buffer solution [for example, 0.02M sodium acetate buffer (pH 5.1)]. Next, the column was developed with the same buffer solution and the unadsorbed material is recovered. To prevent the denaturation of albumin, the above procedure is carried out at a low temperature (usually, 10° C. or below).

In the case of the batch method, the anion exchanger is added to the albumin-containing aqueous solution which has been adjusted to the above-mentioned conditions. After mixing at 10° C. or below for 30 minutes to 2 hours, the solution is separated from the anion exchanger by, for example, centrifugation wherein the supernatant is recovered.

(3) Treatment with cation exchanger

In the formulation of the albumin-containing aqueous solution, which has been purified by the treatment with the anion exchanger as described above, into a pharmaceutical preparation, it is desirable next to treat the preparation with a cation exchanger, after adjusting the pH value and concentration if required, to thereby eliminate contaminating proteins. Any cation exchanger can be used as long as it is an insoluble carrier having a cation exchanging group (for example, sulfo groups or carboxyl groups). Specific examples thereof include cation exchangers commonly used in the art, for example, SP-SEPHADEX ® (dextran bead matrix comprising the sulfopropyl functional group) (a product of Pharmacia), SP-TOYOPEARL ® (vinyl polymer bead matrix comprising the sulfopropyl functional group), TSKgelSP-5PW ® (vinyl polymer bead matrix comprising the sulfopropyl functional group, (each a product of Tosoh Co.) and other known cation exchange resins. From the viewpoint of the efficiency for eliminating contaminating proteins, it is preferable to use strong cation exchangers, such as SP-SEPHAROSE ® (agarose bead matrix comprising the sulfopropyl functional group) and SP-TOYOPEARL ®.

The treatment with the above-described cation exchanger may be carried out by contacting the albumin-containing aqueous solution, which has been purified by the above anion exchanger treatment, with the cation exchanger. The amount of the cation exchanger may be controlled depending on the amount of contaminating proteins in the albumin-containing aqueous solution and the exchanging capacity of the cation exchanger. In general, from 2 to 5 ml, usually about 2 ml, of the cation exchanger is used per gram of albumin. The treatment may be effected either by the column method or by the batch method. The column method is preferable from the view,point of the efficiency of eliminating contaminating proteins.

In the case of the column method, the above-described albumin-containing aqueous solution is adjusted to a pH value of from 4 to 8, preferably from 4.5 to 6.0, more preferably 5.5, and to a salt concentration of from 0.001 to 0.2M, preferably from 0.001 to 0.05M, in terms of sodium chloride. Then the solution is passed through an cation exchange column equilibrated with a buffer solution [for example, 0.02M sodium acetate buffer (pH 5.5)]. Next, the column is developed with the same buffer solution and the unadsorbed material is recovered. To prevent the denaturation of albumin, the above procedure preferably is carried out at a low temperature (usually, 10° C. or below).

In the case of the batch method, the cation exchanger is added to the albumin-containing aqueous solution which has been adjusted to the above-mentioned conditions. After mixing at 10° C. or below for 30 minutes to 2 hours, the solution is separated from the cation exchanger by, for example, centrifugation and the supernatant is recovered.

2. Filling in Preservation Container

The albumin-containing aqueous solution, in which the aluminum content and the contaminating protein content have been reduced by the above-described treatments with the anion exchanger and the cation exchanger, then is adjusted to an appropriate concentration and formulated into a pharmaceutical preparation of the desired form by, for example, filling in a preservation container. Next, the container is heat treated and thus an albumin preparation is obtained.

The preservation container to be used here is not restricted particularly so long as it is a dealkalized soft glass container. The soft glass comprises, for example, from 65 to 75% of $SiO_2$, from 0.5 to 4% of $Al_2O_3$, from 10 to 20% of $Na_2O$, from 1 to 2% of $K_2O$, from 5 to 15% of CaO, 2% or less of $Fe_2O_3$ and from 0.5 to 4% of MgO (cf. for example, "Encyclopaedia Chimica", published by Kyoritsu Shuppan K.K.).

The dealkalization may be effected by, for example, treating with sulfurous acid gas or ammonium sulfate solution.

The above-mentioned heat treatment is effected to inactivate viruses which might invade the albumin preparation during the formulation process. The treatment is carried out by heating the aqueous albumin solution having an albumin concentration of 5 to 30%, usually 5 or 20 to 25%, to a temperature and for a period enough to inactivate the contaminating viruses. For example, it may be heated to from 50° to 70° C., preferably about 60° C., for from 5 to 20 hours, preferably about 10 hours. In the heat treatment, a stabilizer for albumin (for example, N-acetyltryptophan sodium or sodium caprylate) may be added either alone or in the form of a mixture, if required. The albumin stabilizers may be used in an amount of from 20 to 60 mg, preferably 40 mg, per gram of the albumin contained in the preparation.

The aluminum content of the albumin preparation thus obtained is reduced to about 200 ppb (determined by atomic absorption spectrometry, the same will apply hereinafter) or less. In general, a preferable aluminum content of 100 ppb or below can be achieved.

BEST MODE TO PRACTICE THE INVENTION

The following Example and Test Example are given to further illustrate the present invention in greater detail, and not by way of restriction.

EXAMPLE 1

(1) Preparation of Albumin-containing Aqueous Solution

A paste of the fraction V (500 g) obtained by Cohn's cold alcohol fractionation of serum was dissolved in 2.0 liter of cold sterile distilled water and the pH value of the solution was adjusted to 4.6 with acetic acid. After stirring for about 1 hour, the solution was filtered (filter: 0.45 μm) at about −2° C. Another 2.0 liters of cold sterile distilled water were added and the pH value of the mixture was adjusted to 5.1 with 1N sodium hydroxide to thereby obtain an albumin-containing aqueous solution.

(2) Treatment with Anion Exchanger

QAE-TOYOPEARL® (580 ml) was packed into a column [5 cm (diameter)×18 cm (height)] and thoroughly washed with 0.5M sodium chloride. The exchanger was equilibrated with 0.02M sodium acetate (pH 5.1) to obtain an anion exchange column. Then the albumin-containing aqueous solution obtained in the above (1) was passed over the column and the column was washed further with cold 0.02M sodium acetate (pH 5.1, 2 liter). The buffer was collected and the pH value of the mixture was adjusted to 5.5 with 0.8M sodium hydrogen-carbonate.

(3) Treatment with Cation Exchanger

SP-TOYOPEARL® (400 ml) was packed into a column and thoroughly washed with 0.5M sodium chloride. The exchanger was equilibrated with 0.02M sodium acetate (pH 5.5) to obtain a cation exchange column. Then the albumin-containing aqueous solution obtained in the above (2) was passed through the column and further washed with 0.02M sodium acetate (pH 5.1, 1.2 liter). The buffer was collected and the mixture was dialyzed and concentrated with Pellicon to give $A_{280}=149$ (albumin concentration: 28%).

(4) Filling in Container and Heat Treatment

To the albumin-containing aqueous solution obtained in the above (3) was added a stabilizer solution, containing 5.55 g of N-acetyltryptophan and 3.89 g of sodium caprylate in 100 ml, at a ratio of 1.2 ml per 10 ml of said albumin-containing aqueous solution. After adjusting the pH value to 6.85 with 1N sodium hydroxide, the mixture was sterile filtered. Next, the albumin concentration was adjusted to 25% and a defined amount of the solution was pipetted into a soft glass container (50 ml) treated with sulfurous acid gas. Then the container was heated to 60° C. for 10 hours to thereby obtain an albumin pharmaceutical preparation.

The aluminum content of the thus obtained albumin preparation determined by atomic absorption spectrometry was 70 ppb.

TEST EXAMPLE

Changes in aluminum content of an albumin preparation during preservation were compared when using a hard glass container and when using a soft glass container of the present invention. The soft glass container was surface-treated with sulfurous acid gas. Table 1 shows the composition of each preservation glass container.

The albumin-containing aqueous solution purified in accordance with Example 1 (1) to (3) was distributed into the above hard glass container and the soft glass container. Both containers were heated in accordance with Example 1 (4) to prepare an albumin pharmaceutical preparation. Each albumin preparation thus obtained was preserved at 40° C. for 3 months and then the aluminum content thereof was determined by atomic absorption spectrometry. Table 2 shows the results.

TABLE 1

| Component | Hard glass (%) | Soft glass (%) |
|---|---|---|
| $SiO_2$ | 70.0 | 72.6 |
| $B_2O_3$ | 9.7 | 0.1 |
| $Al_2O_3$ | 5.8 | 1.9 |
| $Na_2O$ | 7.8 | 12.6 |
| $K_2O$ | 1.8 | 1.0 |
| CaO | 0.7 | 11.0 |
| $Fe_2O_3$ | 0.05 | 0.04 |
| MgO | 0.1 | 0.2 |
| $SO_3$ | 0.08 | 0.23 |
| ZnO | 1.4 | 0 |
| BaO | 2.6 | 0 |

TABLE 2

| Preservation container | Aluminum content (ppb) | |
|---|---|---|
| | Before filling | After storage |
| Hard glass container | <50 | 120 |
| Soft glass container (invention method) | <50 | <50 |

As the above Table 2 clearly shows, the aluminum content was increased when the hard glass container was used for the preservation, while no increase in the aluminum content was found when using a dealkalized soft glass container for the preservation according to the present invention.

INDUSTRIAL APPLICABILITY

In the method for preserving an albumin preparation of the present invention, a dealkalized soft glass preservation container is used. According to the method of the present invention, the aluminum content of an albumin preparation can be minimized during the validated period of said preparation (30° C. or below, 2 years) and thus a product of a high safety can be provided. When a purified albumin-containing aqueous solution in which the aluminum content has been reduced by treating with an anion exchanger, is used as an albumin-containing aqueous solution, in particular, the aluminum content of the albumin preparation can be reduced to about 200 ppb or below. Hence, because an increase in the aluminum content during preservation is minimized, the aluminum content of the albumin preparation can be maintained at a low level and therefore a highly safe preparation with a long shelf-life can be provided.

We claim:

1. An article of manufacture comprising an aqueous albumin preparation enclosed within a closed soft glass container having an internal dealkalized surface wherein said preparation has less than 200 parts per billion aluminum.

2. The article of claim 1, wherein said soft glass comprises from 65–75% silicon dioxide, from 0.5–4% aluminum oxide, from 10–20% sodium oxide, from 1–2% potassium oxide, from 5–15% calcium oxide, 2% or less iron oxide and from 0.5–4% magnesium oxide.

3. The article of claim 1, wherein said soft glass container is dealkalized by treatment with sulfurous acid gas or an ammonium sulfate solution prior to enclosing said preparation in said container.

4. The article of claim 1, wherein the amount of aluminum is 100 parts per billion or less.

5. The article of claim 1, wherein the albumin is of plasma origin.

6. The article of claim 1, wherein said albumin preparation is treated with an anion exchange medium prior to enclosing said preparation in said container.

7. The article of claim 6, wherein said anion exchange medium comprises a matrix with a $CH_2N^+(CH_3)_3$ functional group or a diethyl[2-hydroxypropyl]aminoethyl functional group.

8. The article of claim 6, wherein said albumin preparation further is treated with a cation exchange medium prior to enclosing said preparation in said container.

9. The article of claim 8, wherein said cation exchange medium comprises a matrix with a sulfopropyl functional group.

10. The article of claim 1, wherein said albumin preparation is exposed to a temperature of at least 50° C. for a time sufficient to inactivate any contaminating virus.

11. The manufacture of claim 10, wherein said albumin preparation further comprises N-acetyltryptophan or sodium caprylate.

* * * * *